US008492420B2

(12) United States Patent  (10) Patent No.: US 8,492,420 B2
Becq et al.  (45) Date of Patent: Jul. 23, 2013

(54) USE OF PURINE DERIVATIVES FOR THE PRODUCTION OF MEDICAMENTS FOR THE TREATMENT OF MUCOVISCIDOSIS AND DISEASES RELATED TO PROTEIN ADDRESSING ERRORS IN CELLS

(75) Inventors: Frédéric Becq, Poitiers (FR); Laurent Meijer, Roscoff (FR)

(73) Assignees: Centre National de la Recherche Scientifique-CNRS, Paris (FR); Universite de Poitiers, Poitiers (FR)

( * ) Notice: Subject to any disclaimer, the term of this patent is extended or adjusted under 35 U.S.C. 154(b) by 247 days.

(21) Appl. No.: 11/786,754

(22) Filed: Apr. 12, 2007

(65) Prior Publication Data

US 2007/0275986 A1  Nov. 29, 2007

Related U.S. Application Data

(63) Continuation of application No. PCT/FR2005/002557, filed on Oct. 14, 2005.

(30) Foreign Application Priority Data

Oct. 15, 2004 (FR) ..................................... 04 10958

(51) Int. Cl.
*A01N 43/50* (2006.01)
*A61K 31/415* (2006.01)

(52) U.S. Cl.
USPC .......................... 514/397; 514/183; 514/263.4

(58) Field of Classification Search
USPC ...................................................... 514/263.4
See application file for complete search history.

(56) References Cited

U.S. PATENT DOCUMENTS

| 6,316,456 | B1 | 11/2001 | Meijer et al. | |
| 2004/0116442 | A1* | 6/2004 | Guzi et al. | 514/252.16 |
| 2005/0004186 | A1* | 1/2005 | Barrett et al. | 514/363 |
| 2008/0076756 | A1 | 3/2008 | Becq et al. | |

OTHER PUBLICATIONS

Hiromura et al., Modulation of apoptosis by the cyclin-dependent kinase inhibitor p27kip1, 1999, The Journal of Clinical Investigation, vol. 103, No. 5, pp. 597-604.*
Becq et al., "Development of Substituted Benzo[c]quinolizinium Compounds as Novel Activators of the Cystic Fibrosis Chloride Channel," The Journal of Biological Chemistry, 274(39), pp. 27415-27425, (1999).
Becq et al., "Pharmacological interventions for the correction of ion transport defect in cystic fibrosis," Expert Opin. Ther. Patents, 14(10), pp. 1465-1483, (2004).
Dormer et al., "Correction of delF508-CFTR activity with benzo(c)quinolizinium compounds through facilitation of its processing in cystic fibrosis airway cells," Journal of Cell Science, 114(22), pp. 4073-4081, (2001).
Egan et al., "Calcium-pump inhibitors induce functional surface expression of ΔF508-CFTR protein in cystic fibrosis epithelial cells," Nature Medicine, 8(5), pp. 485-492 (2002).
Jacobson et al., "Stimulation by Alkylxanthines of Chloride Efflux in CFPAC-1 Cells Does Not Involve $A_1$ Adenosine Receptors," Biochemistry, 34(28), pp. 9088-9094, (1995).
Norez et al., "Rescue of functional delF508-CFTR channels in cystic fibrosis epithelial cells by the α-glucosidase inhibitor miglustat," FEBS Lett. 580, pp. 2081-2086 (2006).
Powell et al., "Therapeutic approaches to repair defects in ΔF508 CFTR folding and cellular targeting," Advanced Drug Delivery Reviews, 54, pp. 1395-1408 (2002).
Vesely et al., "Inhibition of cyclin-dependent kinases by purine analogues," Eur. J. Biochem., 224, pp. 771-786 (1994).
Pedemonte et al., Antihypertensive 1,4-Dihydropyridines as Correctors of the Cystic Fibrosis Transmembrane Conductance Regulator Channel Gating Defect Caused by Cystic Fibrosis Mutations, Mol Pharmacol 68(6):1736-1746 (2005).
Van Goor et al., Rescue of ΔF508-CFTR Trafficking and Gating in Human Cystic Fibrosis Airway Primary Cultures by Small Molecules, Am J Physiol Lung Cell Mol Physiol 290:L1117-1130 (2006).
McKeon, D.J., et al., "Prolonged survival of neutrophils from patients with ΔF508 CFTR mutations", Thorax, vol. 63, No. 7, pp. 660-661 (Jul. 2008) (downloaded on Apr. 23, 2012).
Moriceau, Sandra, et al., "Coronin-1 Is Associated with Neutrophil Survival and Is Cleaved during Apoptosis: Potential Implication in Neutrophils from Cystic Fibrosis Patients", J. Immunol., vol. 182, pp. 7254-7263 (2009) (downloaded May 10, 2012).

* cited by examiner

*Primary Examiner* — Jeffrey S. Lundgren
*Assistant Examiner* — Meghan Finn
(74) *Attorney, Agent, or Firm* — Harness, Dickey & Pierce, P.L.C.

(57) ABSTRACT

The invention relates to the use of purine derivatives for the production of medicaments for the treatment of mucoviscidosis and diseases related to protein addressing errors in cells, said derivatives being of formula (I): where R2, R6 and R9, independently=halogen, a R—NH—, R—NH—NH—, NH$_2$—R'—NH or R—NH—R'—NH— group, where R=straight or branched chain saturated or unsaturated alkyl, aryl, cycloalkyl, or heterocyclyl group, R'=straight or branched chain, saturated or unsaturated alkylene, arylene or cycloalkylene, R and R' each include 1 to 8 carbon atoms optionally substituted with one or more —OH, halogen, amino or alkyl groups, R2 furthermore may be a heterocycle optionally with a straight or branched chain saturated or unsaturated alkyl, aryl or cycloaryl or a heterocycle optionally substituted by one or more —OH, halogen, amino or alkyl groups, R9 furthermore may be a straight or branched chain saturated or unsaturated alkyl, aryl or cycloalkyl and R2 and R9 furthermore may be hydrogen with the exception of 2-(2-hydroxyethylamino)-6-benzylamino-9-methylpurine.

16 Claims, 5 Drawing Sheets

USE OF PURINE DERIVATIVES FOR THE PRODUCTION OF MEDICAMENTS FOR THE TREATMENT OF MUCOVISCIDOSIS AND DISEASES RELATED TO PROTEIN ADDRESSING ERRORS IN CELLS

CROSS-REFERENCE TO RELATED APPLICATIONS

This application is a continuation of PCT/FR2005/002557, filed Oct. 14, 2005, which claims priority to French Application No. 04/10958, filed Oct. 15, 2004. Both of these applications are incorporated by reference herein.

BACKGROUND AND SUMMARY

The invention aims at using purine derivatives for the production of medicaments able to restore addressing of proteins from the endoplasmic reticulum to the plasma membrane. It aims in particular at treating mucoviscidosis.

Mucoviscidosis (CF) is the most common recessive autosomal lethal genetic disease in European and North American populations. The CF gene (locus 7q31) encodes a protein called Cystic Fibrosis Transmembrane Conductance Regulator (CFTR). Mutations of the CF gene cause abnormal transport of water and electrolytes through the cell membrane of various organs such as the lungs, sudoriparousglands, the intestine and the exocrine pancreas. Although there are over 1,000 mutations of the CFTR protein, the most common mutation (70% of patients) is the deletion of a phenylalanine in the NBF1 domain at position 508 (delF508). The main cause of mortality in CF patients is linked to this deletion and leads to infections or pulmonary insufficiency due to an increase in mucus viscosity. Such viscosity causes occlusion of respiratory airways and promotes infections by opportunistic bacteria. Furthermore, an aggravation is observed at the level of the digestive apparatus and the pancreas particularly (patient with pancreatic insufficiency). The CFTR protein is a glycoprotein of 1,480 amino acids, belonging to the ABC superfamily of membrane transporters. CFTR is a chloride ion channel localised in the apical plasma membrane of lung epithelial cells in healthy individuals. CFTR is responsible for trans-epithelial transport of water and electrolytes, thereby allowing hydration of lung airways in healthy individuals.

In CF patients homozygous for delF508 mutation, and more generally for class-II mutations (i.e. producing a protein that is absent from the cell membrane), CFTR is absent from the plasma membrane due to faulty addressing of this protein, which remains in the endoplasmic reticulum (ER). In such cases, hydration of lung airways is no longer functional. The delF508 deletion alters the folding of the NBF1 domain and prevents the full maturation of the protein, which is therefore degraded very early during biosynthesis. However, if the delF508 protein is able to reach the membrane, it works as a chloride ion channel.

One of the keys to treating this disease therefore consists in re-addressing delF508 to the plasma membrane of the cell, where the transport activity of delF508 can be stimulated by physiological agonists. Surprisingly, the inventors showed that derivatives known in particular for their anti-proliferative effect were capable of activating wild-type and mutated forms of CFTR, and inducing the relocation of delF508-CFTR protein to the plasma membrane, thereby restoring its transmembrane transport capacity. Generally speaking, such derivatives can restore a protein addressing error in cells. Furthermore, such derivatives have the advantage of being highly innocuous. The aim of the invention is therefore to provide a new use of these derivatives in order to produce medicaments for the treatment of mucoviscidosis and diseases related to a protein addressing error in cells.

The derivatives used according to the invention are purines substituted at positions 2, 6 and 9. Derivatives of this type have been described as kinase inhibitors. Such derivatives are in particular described in patent FR 95 14 237 and the patents and patent applications corresponding to PCT/FR96/01905, or in the article by Vesely et al, 1994, Eur. J. Biochem., 224, 771-786 II. The 2-(2-hydroxyethylamino)-6-benzylamino-9-methylpurine, commonly called olomoucine, is not within the scope of the invention.

The derivatives concerned are represented by formula I

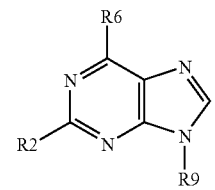

where,

R2, R6 and R9, identical or different from each another, represent a halogen atom, an R—NH—, R—NH—NH—, NH$_2$—R'—NH— or R—NH—R'—NH— group, wherein R is a straight or branched chain saturated or unsaturated alkyl group, an aryl or cycloalkyl group, or a heterocycle, and R' is a straight or branched chain saturated or unsaturated alcoylene group, or an arylene or cycloalcoylene group, R and R' each including 1 to 8 carbon atoms and being substituted, as the case may be, with one or more —OH, halogen, amino or alkyl groups, R2 also possibly representing a heterocycle with, as the case may be, a straight or branched chain saturated or unsaturated alkyl group, an aryl or cycloaryl group, or a heterocycle, possibly substituted with one or more —OH, halogen, amino or alkyl groups, R9 also possibly representing a straight or branched, saturated or unsaturated alkyl group, an aryl or cycloalkyl group, R2 and R9 also possibly representing a hydrogen atom, with the exception of olomoucine.

The invention aims in particular at using derivatives of formula I supra, where

R2 is chosen among the 3-hydroxypropylamino, 1-ethyl-2-hydroxyethylamino, 5-hydroxypentylamino, 1-D,L hydroxymethylpropylamino, aminoethylamino, 2-bis (hydroxyethyl)amino, 2-hydroxypropylamino, 2-hydroxyethylamino, chloro, R-hydroxymethyl-pyrrolidinyl, benzylaminohydroxyethyl, R,S-aminohydroxyhexyl, S amino-2-phenylhydroxyethyl, R amino-3-phenylhydroxypropyl, R,S aminohydroxypentyl, R aminohydroxypropyl, S aminohydroxypropyl, R(−)N-pyrrolidine hydroxymethyl groups, R9 is chosen among methyl, isopropyl or cyclopentyl, and R6 is chosen among benzylamino, 3-iodo-benzylamino, or isopentenylamino groups, when R9 represents an isopropyl group, cyclohexylamino, cyclomethylamino, or 3-hydroxybenzylamino groups, when R9 represents a methyl group, and a benzylamino group, when R9 represents a cyclopentyl group.

These derivatives correspond to optical isomers and racemic mixtures, or as the case may be to geometric isomers. They more specifically involve 2-(R,S)(1-ethyl-2-hydroxyethylamino)-6-benzylamino-9-isopropylpurine or 2-(R)-(1-ethyl-2-hydroxyethylamino)-6-benzylamino-9-isopropylpurine, or even 2-(S)(1-ethyl-2-hydroxyethylamino)-6-benzylamino-9-isopropylpurine.

Said purine derivatives have the capacity to restore CFTR protein addressing to the plasma membranes of the cells and therefore constitute highly interesting compounds for the treatment of pathologies linked to such addressing errors. As illustrated by the various examples, they are particularly efficient for inducing the relocation of the delF508-CFTR protein to the membrane in mucoviscidosis, where this protein is retained in the endoplasmic reticulum, and thus restoring its trans-membrane transport capacity.

When developing medicaments, therapeutically efficient quantities of the active principles are mixed with pharmaceutically acceptable vehicles for the administration route chosen. Such vehicles may be solid or liquid. Thus, for oral administration, medicaments are prepared in the form of gelatine capsules, tablets, sugar coated tablets, capsules, pills, drops, syrups and similar. Such medicaments may contain 1 to 100 mg of active principle per unit. For parenteral administration (intravenous, subcutaneous, intramuscular injection), the medicaments are presented in the form of sterile or sterilisable solutions. They may also be in the form of suspensions or emulsions. The medicaments of the invention are more particularly administered in the form of aerosols.

Doses per administration unit may vary from 1 to 50 mg of active principle. The daily posology is chosen so as to obtain a final concentration not exceeding 100 μM of purine derivative in the blood of patients under treatment. Other characteristics and advantages of the invention will be described in the results reported below in order to illustrate the invention.

BRIEF DESCRIPTION OF THE DRAWINGS

In these examples, reference is made to FIGS. 1 to 6, which show.

DETAILED DESCRIPTION

Figure 1:
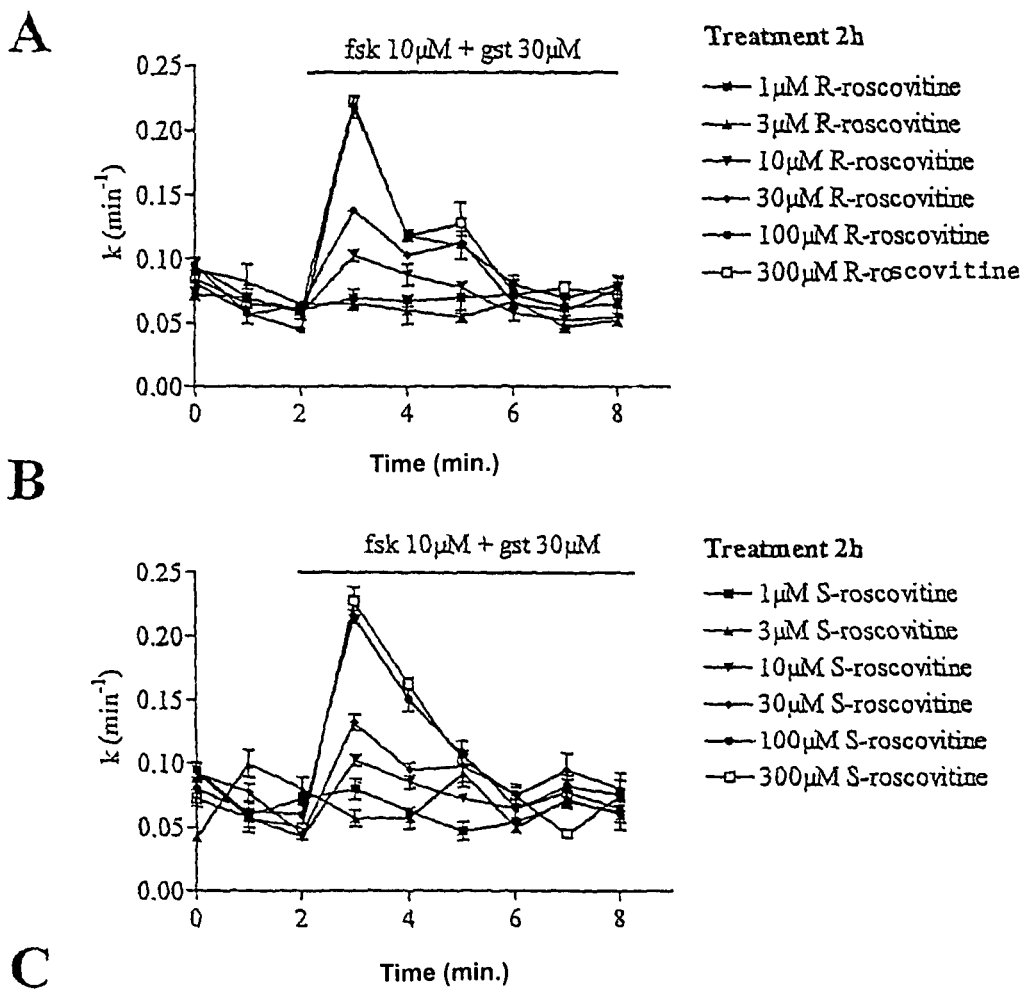
FIG. 1: Effect of roscovitine on delF508 addressing in CF15 cells (1A); on CFTR activity in calu-3 cells (1B); on CFTR addressing in Calu-3 cells (1C)
Figure 1:
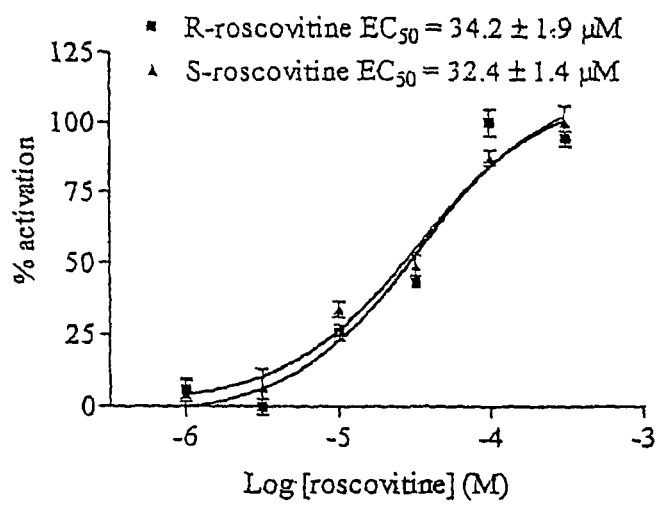
Figure 2:
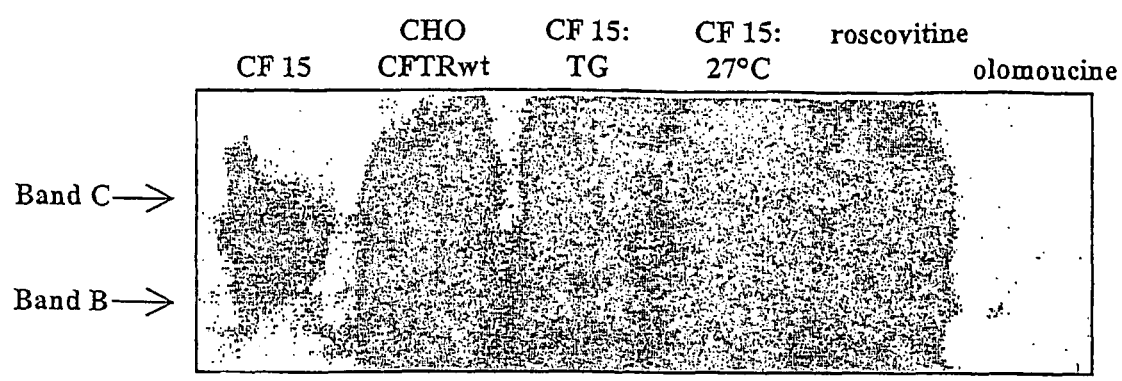
FIG. 2: Results of immunoprecipitation and Western-Blot analyses.

Materials and Methods
M1. Cell Culture
CHO-WT cells: CHO (Chinese Hamster Ovary) cells are fibroblasts transfected with the wild-type CFTR gene (CFTR-WT). These cells will therefore overexpress the CFTR protein.

Culture medium: MEM alpha medium (GIBCO)+7% foetal calf serum+0.5% penicilline/streptomycin+100 μM methotrexate (amethopterine, Sigma).

CF15 cells: CF15 cells are human nasal epithelial cells expressing the ΔF508-CFTR gene.

Culture medium: DMEM+HAM F12 medium+10% FCS+ 0.6% penicilline/streptomycin+growth factors (5 μg/ml insulin, 5 μg/ml transferrin, 5.5 μM epinephrin, 0.18 mM adenine, 10 ng/ml EGF, 2 nM T3, 1.1 μM hydrocortisone).

Calu-3 cells: Calu-3 cells are human lung epithelial cells expressing the wild-type CFTR gene.

Culture medium: DMEM/F12 medium with glutamax+7% foetal calf serum+1% penicillin/streptomycin.

M2. Immunolabelling

Immunolabelling allows visualising the cellular localisation of the CFTR protein by means of an anti-CFTR primary antibody (Ab), and a secondary Cy3-labelled fluorescent antibody directed against the primary antibody. The cells are first seeded on cover slips in an appropriate culture medium. The cells are then washed 3 times with TBS (157 mM NaCl, 20 μM Tris base, pH 7.4) for 5 min. each time and then fixed by adding 3% TBS-paraformaldehyde for 20 min. After 3 washes with TBS (5 min. each), the cells are incubated with 0.1% TBS-triton (10 min) to make holes in the cell membrane, and then washed 3 times with TBS before being exposed to 0.5% TBS-BSA-0.05% saponin for 1 hr. The cells are then incubated with the primary anti-CFTR C terminal antibody (2 μg/ml) for 1 hr. The cells are washed 3 times (5 min. each) with TBS-BSA-saponin before incubating with the GAM-cy3 secondary antibody (1/400) for 1 hr. After 2 TBS washes (5 min. each), the nuclei are labelled by incubating with Topro3 (1/1,000) for 5 min. Finally, the cover slips can be mounted on a glass slide after 3 final TBS washes (5 min. each). The slides are analysed with a confocal microscope (Bio-Rad) using laser excitation at appropriate wavelengths. In order to differentiate Cy3 from Topro3 labelling, the colour of the Topor3 fluorescence has been changed to blue (colour of the nuclei).

M3. Efflux of Radiotracers

Measurements of chloride ion transport in the cells were performed using the radioactive iodide efflux technique (Becq and al., 1999; Dormer and al., 2001). The $^{125}$I tracer is incorporated into the intracellular milieu. The quantity of radiotracer coming out of the cell is then measured after adding various pharmacological agents. Iodide is used as a tracer of chloride ion transport. $^{125}$I has the advantage of being short-lived compared to other markers such as $^{35}$CI (respective half-lives: 30 days and 300,000 years).

The cells are incubated in an appropriate medium in 24-well plates. The cells are rinsed twice with efflux medium (136.6 mM NaCl, 5.4 mM KCl, 0.3 mM KH$_2$PO$_4$, 0.3 mM NaH$_2$PO$_4$, 4.2 mM NaHCO$_3$, 1.3 mM CaCl$_2$, 0.5 mM MgCl$_2$, 0.4 mM MgSO$_4$, 10 mM HEPES, 5.6 mM D-glucose) in order to eliminate dead cells, which release radioactivity in an anarchic fashion. The cells are then incubated with a 500-μl load (1 μCi/ml $^{125}$INa) for 30 min for CHO-WT or 1 hr for CF15 and Calu-3 cells. The iodide equilibrates on either side of the cell membrane. The following steps are performed using a MultiPROBE probe (Packard): the loading medium is rinsed with efflux medium in order to eliminate extracellular radioactivity. The supernatant is collected every minute into haemolysis tubes and the medium is replaced by an equivalent volume of medium (500 μl). No drug is added to the samples taken in the first three minutes in order to obtain a stable baseline characterising the passive exit of I ions. The 7 samples that follow are obtained in the presence of the molecule to be tested. At the end of the experiment, the cells are lysed by adding 500 μl of 0.1 N NaOH/0.1% SDS (30 min), which allows determining the level of radioactivity remaining inside the cell. The radioactivity present in the haemolysis tubes is measured as counts per minute (cpm) using a Cobra II gamma counter (Packard). The results (cpm) are expressed as velocity of radioactive iodide efflux (R) according to the formula: R (min$^{-1}$)=[ln($^{125}$I t$_1$)−ln($^{125}$I t$_2$)]/(t$_1$−t$_2$) where $^{125}$I t$_1$=at time t$_1$ and $^{125}$I t$_2$=at time t$_2$. This iodide flux is represented by a graph. In order to quantify the iodide efflux due to administration of the tested molecule, the relative flux is calculated as follows in order to ignore the basal flux: Relative velocity (min$^{-1}$)=Rpeak−Rbasal. Finally, these results are normalised in order to compare the effect of one drug versus another. The results are presented in the form of a mean +/−SEM. Student's statistical test is used to compare the effect of the various drugs with the controls (the corresponding P<0.01 values are considered to be statistically significant).

M4. Cytotoxicity Test

The MTT cytotoxicity test is a calorimetric test based on the capacity of mitochondrial dehydrogenases to metabolise MTT (a yellow tetrazolium salt) into formazan (purple). The absorbance is proportional to the concentration of converted dye and can then be measured by spectrophotometry. The cells are incubated in 96-well microplates in the presence of the agent to be tested for 2 hours. Three controls are performed: 100% live cells (cells without any agent); 0% live cells (cells left under normal atmosphere); blank (medium without cells). The cells are rinsed with RPMI medium without phenol red in order for the colour of the medium not to interfere with absorbance measurements. The cells are then incubated for 4 hours with 100 μl RPMI solution supplemented with MTT (0.5 mg/ml). The medium is eliminated and 100 μl DMSO is added to dissolve the converted dye (formazan). The absorbance is measured by spectrophotometry at 570 nm (purple); 630 nm (background noise). In order to ignore the background noise, the following calculation is performed: DO$_{reelle}$=DO$_{570nm}$−DO$_{630nm}$. The results are then normalised with respect to the controls (100% and 0% live cells) and presented in the form of a mean +/−SEM.

Results

R1. Effect of Roscovitine on delF508 Addressing in CF15 Cells.

The study of delF508-CFTR protein addressing is performed in the laboratory by using a combination of pharmacological, cellular imagery, biochemical and electrophysiological tests on CF15 human lung epithelial cells homozygous for the delF508 deletion. Results of immunoprecipitation and Western-Blot analyses of non mutated CFTR from wild-type CHO cells and delF508 cells treated for 2 hrs with 100 μM of the tested compound (FIG. 3C) or untreated cells (control). CF15 cells treated for 24 hrs at 27° C. (FIG. 3B) or for 2 hrs with 10 μM thapsigargin (TG) were used as a positive control.

For each experiment, the addition of a cocktail (10 μM Forskoline+30 μM Genisteine) allows activation of the CFTR when the latter is localised in the membrane. This allows an iodide efflux to be observed if delF508 addressing has been restored. The results, presented in the form of a histogram, were normalised with respect to a standard treatment (treatment of the cells with 250 μM MPB-91 for 2 hrs), considered to represent 100% CFTR activity. The results obtained show that treatment of CF15 cells with the two forms (R and S) of roscovitine for 2 hrs at 37° C. restores addressing of the delF508 protein and allows it to function as an ion transporter (FIG. 1).

Figure 3:
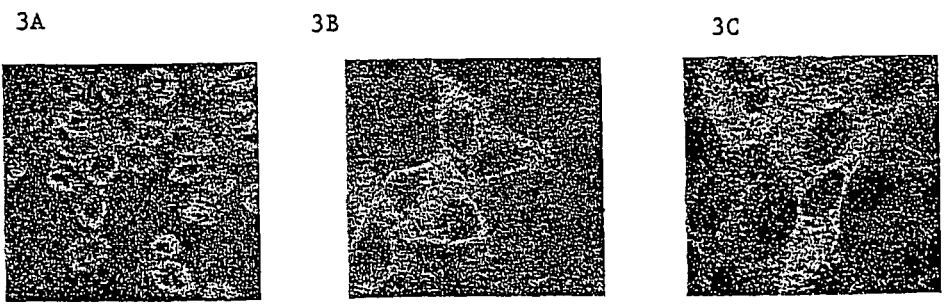
FIGS. 3A to 3C: Immunolocalisation of delF508-CFTR after a 2-hr treatment or in the absence of treatment.

When the cells are not treated, the delF508 protein is not localised in the membrane and no iodide efflux is observed as a result of stimulation with the 10 μM Forskoline+30 μM Genisteine cocktail. The Ec50 (molecular concentration giving 50% of maximal efficiency) for roscovitine was found to be 34±1.9 μM (R-Roscovitine, FIGS. 1A, C) and 32±1.4 (S-Roscovitine, FIGS. 1B, C) (n=4, in each case). Cellular imagery showed that the delF508 protein was localised in the plasma membrane compartment after treatment with roscovitine. FIGS. 3A to 3C also illustrate the immunolocalisation of delF508-CFTR after 2 hrs of treatment with roscovitine or in the absence of treatment. This involves confocal visualisation of CFTR-delF508 in CF15 cells using a mouse anti-CFTR monoclonal antibody. CF15 cells treated for 24 hrs at 27° C. were used as a positive control (FIG. 3A).

Figure 4:
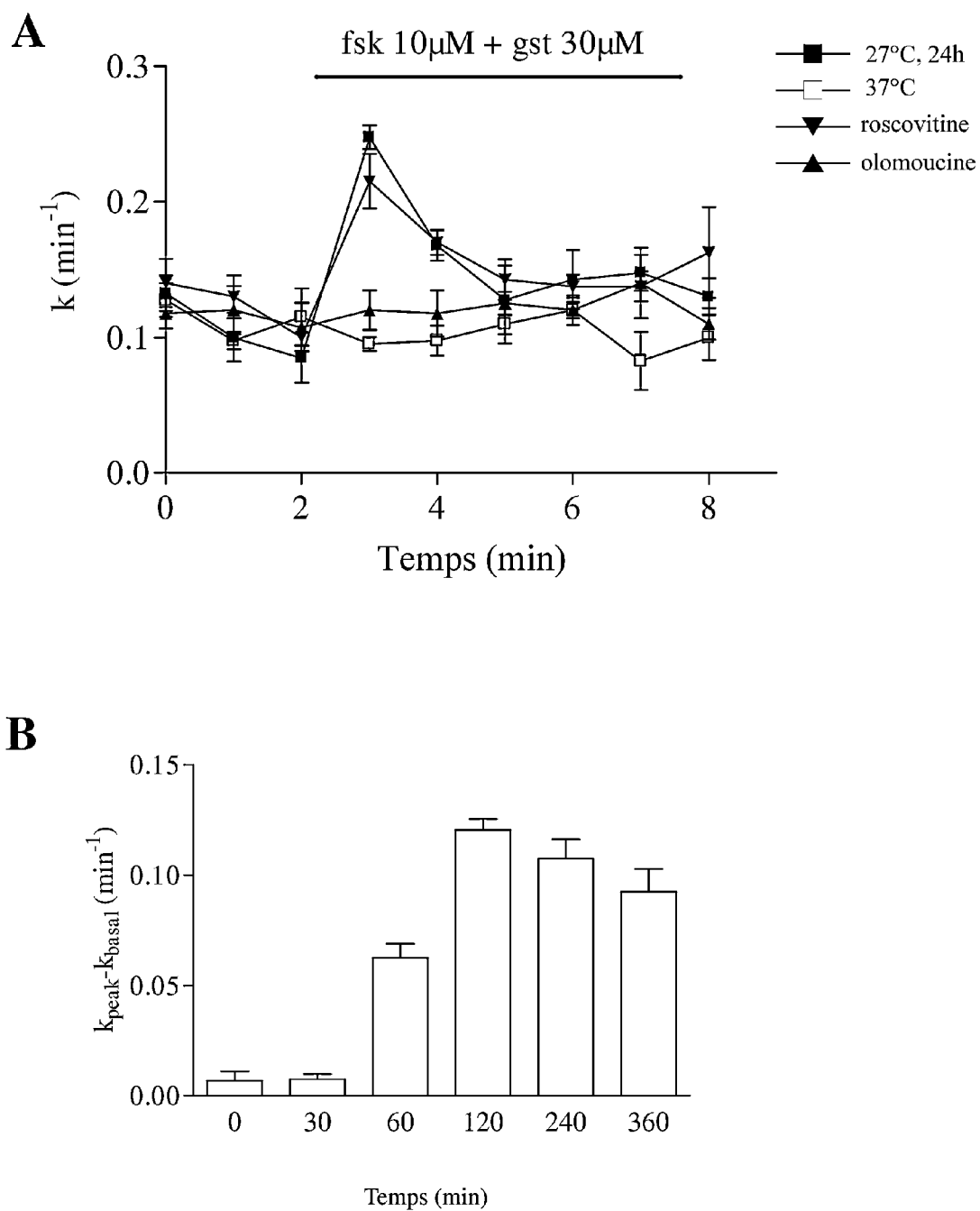
FIGS. 4A and 4B: Activation of delF508 in CF15 cells after treatment with CFTR-T1 (CFTR-T1 designating roscovitine) and response to roscovitine as a function of incubation time.

FIG. 4A illustrates the activation of delF508-CFTR in CF15 cells after treatment with roscovitine. The iodide efflux was observed after 2 hrs of incubation with 100 μM of the tested compound or in the absence of treatment. CF15 cells treated for 24 hrs at 27° C. were used as a positive control and untreated CF15 cells as a negative control (37° C.).

FIG. 4B shows that the response to roscovitine depends on the incubation time. Roscovitine (100 μM) was used for treating CF15 cells. The cells were then stimulated with 10 μM fsk+30 μM gst.

Figure 5:
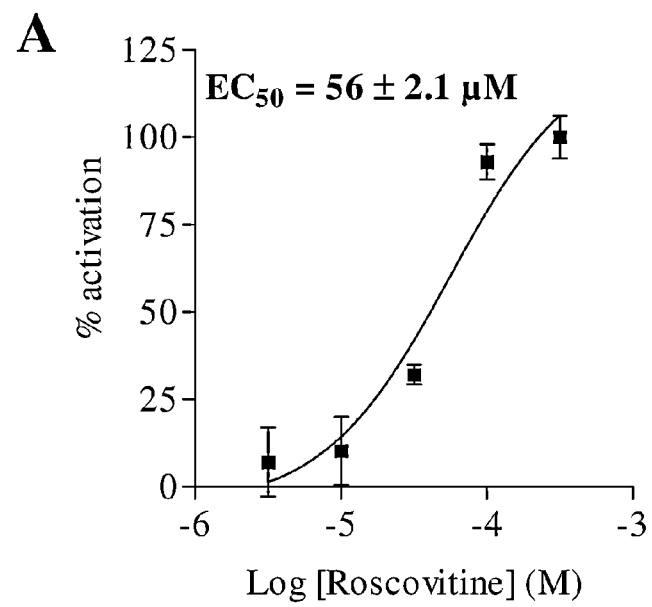
FIGS. 5A and 5B: Percentage of activation as a function of the roscovitine concentration and pharmacological profile of CFTR channels in CF15 cells after incubation with roscovitine.
Figure 5:
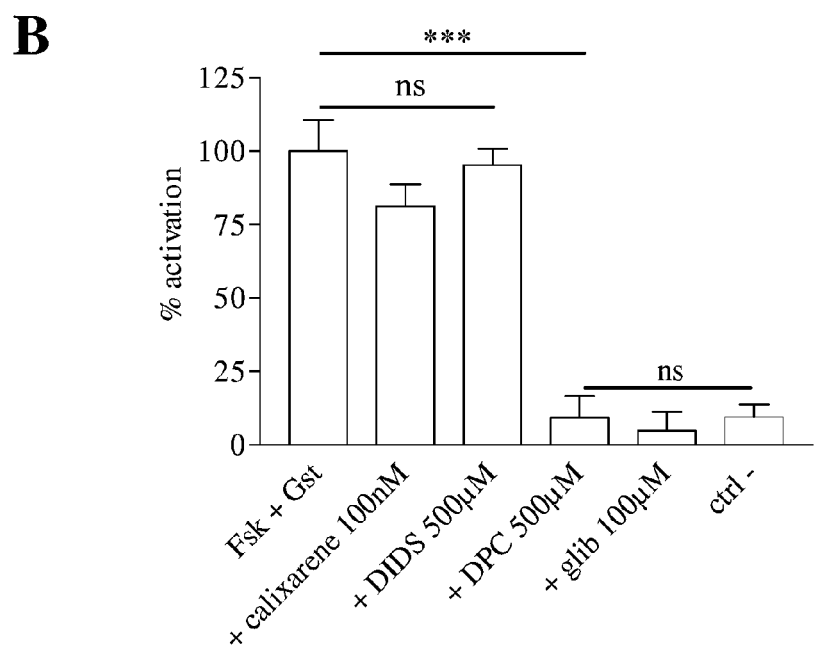

FIG. 5A shows the dose-response results after 2 hrs of treatment with roscovitine. FIG. 5B shows the pharmacological profiles of CFTR channels in CF15 cells after 2 hrs of incubation with 100 μM of roscovitine.

These results show that after treatment with roscovitine, the following is observed:

maturation of delF508-CFTR (band C appears in the Western-Blot) after treatment with CFTR-T1, correct delF508-CFTR relocation to the plasma membrane, and maximal correction of delF508-CFTR chloride ion channel function after 2 hrs of treatment.

Figure 6:
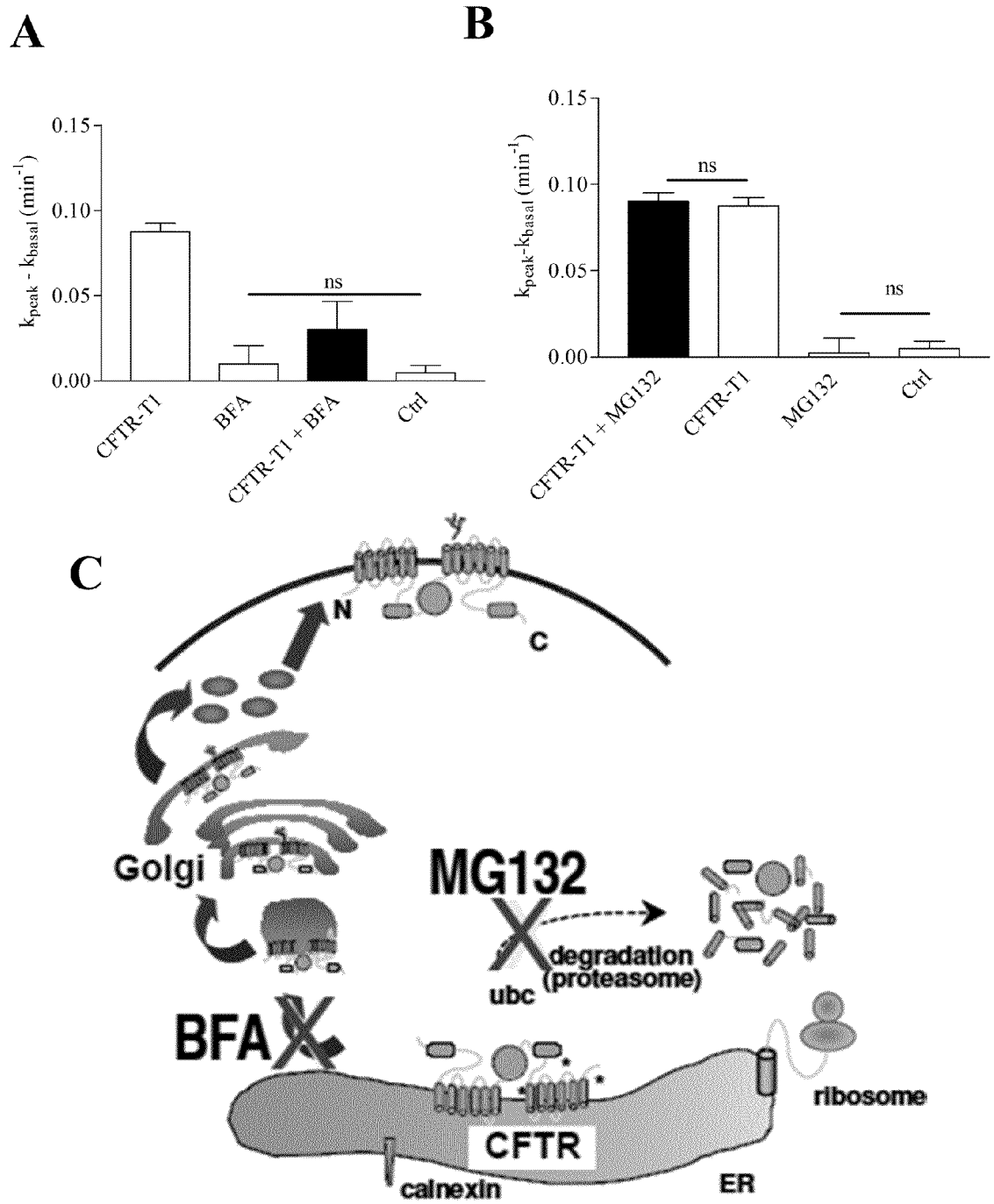
FIG. 6: Competition between CFTR-T1 and the ER chaperon machinery for delF508-CFTR addressing.

The competition between CFTR-T1 and the ER chaperone machinery is illustrated by FIGS. 6A and 6B. FIG. 6A illustrates the inhibition of CFTR-T1 action by Brefeldine A (BFA), an inhibitor of the ERGIC vesicular traffic, which shows that roscovitine induces readdressing of the delF508-CFTR protein. FIG. 6B shows that no modulation is observed in the presence of MG132, a proteasome inhibitor, which shows there is competition between roscovitine and MG132.

The table below summarises the roscovitine and ER chaperone machinery competition experiments performed by the iodide efflux technique.

inhibition, ** P<0.01, * P<0.1, ns P>0.1 (Student's t-test)

| | BFA 20 μM | Tunica-mycine 10 μM | Swain-sonine 100 μM | Castano-spermine 100 μg/l | Thapsi-gargine 10 μM | MG132 20 μM | Geldana-mycine 2.5 μg/ml |
|---|---|---|---|---|---|---|---|
| Potentiation of the CFTR-T1 effect | — | ** | ** | * | * | ns | ns |
| | | Inhibitors of glycosylation | | Inhibitors of calnexin | | Degradation pathway of inhibitors | |

— inhibition, ** P < 0.01, * P < 0.1, ns P > 0.1 (Student's t-test)

These results show that roscovitine induces delF508-CFTR readdressing, inhibits the CFTR-T1 degradation pathway and is able to modulate the interaction between CFTR-T1 and calnexin (calcium-dependent mechanism).

R2. Effect of Roscovitine on CFTR Activity in Calu-3 Cells

In order to show that the effect of roscovitine is specific for delF508 addressing and does not alter other chloride channels, roscovitine was tested as a potential activator in Calu-3 cells. These results were obtained using the iodide efflux technique. The controls used were forskoline (5 μM, n=8) and MPB-91 (250 μM, n=8). Roscovitine (n=8) was not found to be an activator of wild-type CFTR or any other anionic transporter in these cells (no significant difference).

R3. Effect of Roscovitine on CFTR Addressing in Calu-3 Cells

In order to show that the effect of roscovitine is specific to delF508 addressing, roscovitine was tested as a modulator of wild-type CFTR addressing in Calu-3 cells. These results were obtained by measuring iodide efflux in Calu-3 cells treated for 2 hrs with roscovitine (100 μM). The CFTR activity under such experimental conditions is not significantly different from the controls. These results demonstrate that roscovitine does not affect the addressing pathway of the wild-type CFTR or other chloride channels, nor does it alter CFTR activity in non-CF human lung epithelial cells.

R4. Cytotoxicity of Roscovitine

In order to test the cytotoxicity of roscovitine, CHO-WT cells were incubated for 2 hrs with different concentrations of inhibitors before being tested for viability with MTT. The results show that the cells are viable at all concentrations of roscovitine. Therefore, this molecule does not present any cell cytotoxicity.

Efflux tests revealed that roscovitine allows relocation of the delF508-CFTR protein to the membrane and therefore represents a pharmacological mean of re-addressing delF508 in human lung epithelial cells. A 2-hr treatment with 100 μM of roscovitine results in the appearance of the mature CFTR band (as shown by the immunoprecipitation and western-blot techniques), indicating that roscovitine allows the liberation of the delF508-CFTR protein from the ER and its maturation in the Golgi apparatus. Immunofluorescence experiments confirmed that a 2-hr treatment with 100 μM of roscovitine allowed relocation of the delF508-CFTR protein to the membrane. Finally, iodide efflux and patch-clamp experiments on whole cells showed that the readdressed protein was functional. A 2-hr treatment with roscovitine gives an $EC_{50}$ of 56 μM and allows maximal readdressing.

In addition, competition experiments to determine the mechanism of action of roscovitine have shown that roscovitine competed with inhibitors of calnexin/delF508-CFTR binding as well as inhibitors of the degradation pathway. These various results show that roscovitine can correct the delF508-CFTR protein addressing defect. Treatment of CF cells with roscovitine should therefore allow interference with the capacity of the control machinery to interact with and retain the delF508-CFTR protein in the endoplasmic reticulum, via inhibition of calnexin and the chaperon molecules involved in the degradation pathway.

EXAMPLE OF FORMULATION

An inhalation solution is prepared with an ampoule spray starting with sodium chloride, dehydrated calcium chloride and water for injectable preparations. Roscovitine is then added as active ingredient. The solution is formulated in 2.5-ml ampoules. Ampoules including 5, 10 mg or 20 mg of roscovitine can be prepared in this way.

Bibliography

BECQ et al. (1999) Journal of Biological Chemistry 274, 27415-27425.

DORMER et al. (2001) Journal of Cell Science 114, 4073-4081.

The invention claimed is:

1. A method of treating mucoviscidosis comprising administering to a patient having a deletion at position 508 of the CFTR protein (delF508) a therapeutically effective amount of a composition comprising a purine derivative represented by formula (I):

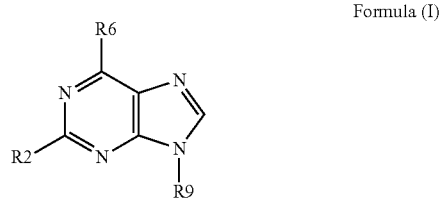

Formula (I)

where R2 comprises 1-ethyl-2-hydroxyethylamino, R6 comprises benzylamino and R9 comprises isopropyl.

2. The method of claim 1, wherein said composition comprises a compound selected from 2-(R,S) (1-ethyl-2-hydroxyethylamino)-6-benzylamino-9-isopropylpurine, 2-(R)-(1-ethyl-2-hydroxyethylamino)-6-benzylamino-9-isopropylpurine, and/or 2-(S) (1-ethyl-2-hydroxyethylamino)-6-benzylamino-9-isopropylpurine.

3. The method of claim 1, wherein said administering comprises delivering said composition to the patient in the form of gelatine capsules, tablets, sugar coated tablets, capsules, aerosols, solutions, drops and/or syrups.

4. A method of claim 1, wherein said patient is a human.

5. The method of claim 1, wherein said administering comprises delivering said composition to the patient parenterally in the form of a solution.

6. The method of claim 1, wherein said administering comprises delivering said composition to the patient in the form of an aerosol.

7. A method of treating mucoviscidosis related to a delF508-CFTR protein addressing error, the method comprising administering to a patient having a deletion at position 508 of the CFTR protein (delF508) a therapeutically effective amount of a purine derivative of formula (I) comprising:

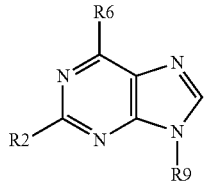

Formula (I)

where,
R2 comprises 1-ethyl-2-hydroxyethylamino, R6 comprises benzylamino, and
R9 comprises isopropyl, wherein the therapeutically effective amount enhances addressing of the delF508-CFTR protein to a cellular plasma membrane for functioning as a chloride ion channel for treating mucoviscidosis, for the hydration of lung airways.

8. The method of claim 7 wherein the derivatives correspond to optical isomers and racemic mixtures, or geometric isomers.

9. The method of claim 7, wherein the derivatives are chosen from 2-(R,S) (1-ethyl-2-hydroxyethylamino)-6-benzylamino-9-isopropylpurine, 2-(R)-(1-ethyl-2-hydroxyethylamino)-6-benzylamino-9-isopropylpurine, and/or 2-(S) (1-ethyl-2-hydroxyethylamino)-6-benzylamino-9-isopropylpurine.

10. The method of claim 7, wherein said administering comprises delivering said purine derivative in the form of gelatine capsules, tablets, sugar coated tablets, capsules, aerosols, solutions, drops and/or syrups.

11. A method of treating a delF508-CFTR protein addressing error comprising:
administering to a patient having a deletion at position 508 of the CFTR protein (delF508) an effective amount of a purine derivative of formula (I) comprising:

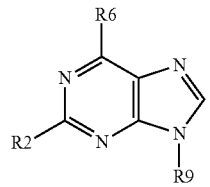

Formula (I)

where,
R2 comprises 1-ethyl-2-hydroxyethylamino, R6 comprises benzylamino, and
R9 comprises isopropyl, wherein the effective amount enhances addressing of the delF508-CFTR protein to a cellular plasma membrane, for the hydration of lung airways.

12. The method of claim 11 wherein the derivatives correspond to optical isomers and racemic mixtures, or geometric isomers.

13. The method of claim 11, wherein the derivatives are chosen from 2-(R,S) (1-ethyl-2-hydroxyethylamino)-6-benzylamino-9-isopropylpurine, 2-(R)-(1-ethyl-2-hydroxyethylamino)-6-benzylamino-9-isopropylpurine, and/or 2-(S) (1-ethyl-2-hydroxyethylamino)-6-benzylamino-9-isopropylpurine.

14. The method of claim 11, wherein said administering comprises delivering said purine derivative in the form of gelatine capsules, tablets, sugar coated tablets, capsules, aerosols, solutions, drops and/or syrups.

15. The method of claim 11, wherein said administering comprises delivering the purine derivative parenterally to the patient in the form of a solution.

16. The method of claim 11, wherein said administering comprises delivering the purine derivative to the patient in the form of an aerosol.

* * * * *